US00PP28468P3

(12) United States Plant Patent
Bradford et al.

(10) Patent No.: US PP28,468 P3
(45) Date of Patent: Oct. 3, 2017

(54) PLUM TREE NAMED 'PLUMCANDY XIII'

(50) Latin Name: *Prunus salicina*
Varietal Denomination: Plumcandy XIII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 32 days.

(21) Appl. No.: 14/757,252

(22) Filed: Dec. 11, 2015

(65) Prior Publication Data

US 2017/0172024 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP14,196 P2 9/2003 Bradford
PP14,220 P2 10/2003 Bradford

*Primary Examiner* — Keith Robinson

(57) ABSTRACT

The present invention relates to a plum tree, *Prunus salicina*, and more particularly to a new and distinct variety broadly characterized by a large size, vigorous, hardy, and somewhat irregularly productive tree. Being self-unfruitful, the present variety requires cross pollination from another plum that blooms during the mid season, such as 'Yummyrosa' plum (U.S. Plant Pat. No. 13,476). The fruit matures under the ecological conditions described in mid to late October, with first picking on Oct. 16, 2015, and has the ability to hang firm on the tree for another three weeks. The fruit is uniformly medium in size, full red in skin color, freestone in type, purely yellow in flesh color, very firm in texture, juicy, typically 22 to 24 brix, and excellent in flavor.

1 Drawing Sheet

Botanical classification: *Prunus salicina.*
Variety denomination: 'PLUMCANDY XIII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumcandy XIII'

During a typical blooming season we isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2004 one such house containing 'Plumsweettwo' (U.S. Plant Pat. No. 14,196) plum was crossed in this manner. To pollinate this plum tree, we selected bouquets from several sources of plum trees without keeping specific written details. Upon reaching maturity the fruit from this plum tree was harvested, and the seeds were removed, cracked, stratified and germinated as a group with the label "H15". They were grown as seedlings on their own root in our greenhouse and upon reaching dormancy transplanted to a cultivated area of our experimental orchard located near Le Grand, Calif. in Merced County (San Joaquin Valley). During the summer of 2009 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Plumsweettwo' (U.S. Plant Pat. No. 14,196), by being self-unfruitful and by producing plums that are very sweet in flavor, firm in texture, and full red to purple in skin color, but is very distinguished therefrom by producing plums that are yellow instead of full red flesh color, that are larger in size, that are freestone instead of clingstone in type, and that mature about ninety days later.

The present variety is most similar to 'September Yummy' (U.S. Plant Pat. No. 14,220) plum by having a large tree, by being self-unfruitful, and by producing plums that are nearly full red with moderate freckling in skin color, mostly yellow in flesh color, juicy, firm in texture, but is distinguished therefrom by being more irregular in setting and by producing plums that are sweeter in flavor, that are oblate instead of globose in shape, and that ripen about thirty days later.

SUMMARY OF VARIETY

The present plum variety is characterized by a large size, vigorous, hardy, and somewhat irregularly productive tree. Being self-unfruitful, the present variety requires cross pollination from another plum that blooms during the mid season, such as 'Yummyrosa' plum (U.S. Plant Pat. No.

13,476). The fruit matures under the ecological conditions described in mid to late October, with first picking on Oct. 16, 2015, and has the ability to hang firm on the tree for another three weeks. The fruit is uniformly medium in size, full red in skin color, freestone in type, purely yellow in flesh color, very firm in texture, juicy, typically 22 to 24 brix, and excellent in flavor.

DRAWING

The accompanying photograph exhibits four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Oct. 27, 2015, on the original tree during its eleventh growing season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

TREE

Size: Large, reaching and maintaining a height of 14' [4.27 m.] and a spread of 7' [2.13 m.] after eleven growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to Perpendicular V type.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Moderately productive, thinning usually necessary.

Fertility: Self-unfruitful, requiring cross pollination by a suitable early to mid-seasonal blooming plum, such as 'Yummyrosa' plum (U.S. Plant Pat. No. 13,476).

Bearing: Irregular bearer, weather dependent.

Trunk:

*Size*.—Medium, reaching a maximum diameter of 5¼" [133.4 mm.] after the eleventh growing season.

*Texture*.—Medium roughness.

*Bark color*.—A Grayish brown [61. gy.Br] and Moderate brown [58. m.Br] variegation with Dark grayish brown [62. d.gy.Br] crevices present.

*Lenticels*.—Approximate Number Per Square Inch: 5. Color: Brownish orange [54. brO]. Average Size: ¼" [6.4 mm.] in length. The width is typically one fourth as much as the length. Shape: Eye-shaped.

Branches:

*Size*.—Medium, diameter of scaffold is 3¼" [82.6 mm.] measured 12" above the crotch, diameter of first hanger is 1¼" [31.8 mm.] measured 6" from the main scaffold.

*Texture*.—Smooth on first and second year wood, increasing roughness with age.

*Color*.—1st Year Wood Topside: Grayish red [19. gy.R]. 1st Year Wood Underside: Brilliant yellow green [116. brill.YG]. 2nd Year Wood: A Light brown [57. l.Br] with a Deep yellow green [118. deep YG] permeating through. Older Wood: A Light brownish gray [63. l.brGy] and Dark brown [59. d.Br] variegation.

*Lenticels*.—Approximate Number Per Square Inch: 20. Color: Light yellowish brown [76. l.yBr]. Average size: 1/16" [1.6 mm.] in length. The width is typically one fourth as much as the length. Shape: Eye-shaped.

Leaves:

*Size*.—Large to medium. Average Length: 4 7/16" [112.7 mm.]. Average width: 2⅛" [54 mm.].

*Arrangement*.—Alternate.

*Thickness*.—Medium.

*Form*.—Elliptical.

*Apex*.—Acuminate.

*Base*.—Acute with an average angle base angle of 70 degrees.

*Surface*.—Smooth on both sides.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Vein color*.—Brilliant greenish yellow [98. brill.gY].

*Petiole*.—Average Length: ⅞" [22.2 mm.]. Average Thickness: 1/16" [1.6 mm.]. Color: Brilliant greenish yellow [98. brill.gY] becoming Grayish greenish yellow [105. gy.gY] with exposure to sunlight.

*Stipules*.—Number: 2 per leaf, up to 6 per growing tip. Average Length: ¼" [6.4 mm.]. Color: Brilliant yellow green [116. brill.YG] becoming Dark grayish reddish brown [47. d.gy.rDr] with age.

*Glands*.—Number: 1 to 4, most often 2. Position: Usually alternate, positioned on the petiole and at the intersection of petiole and base of blade. Form: Globose. Size: Small, 1/64" [0.4 mm.] in diameter. Color: Brilliant greenish yellow [98. brill.gY] becoming Dark brown [59. d.Br] in the center with age.

*Leaf buds*.—Pointed.

Flower buds:

*Hardiness*.—Hardy, with respect to central California blooming season.

*Diameter*.—Typically 3/16" [4.8 mm.] 1 week before bloom.

*Length*.—Typically ⅜" [9.5 mm.] 1 week before bloom.

*Form*.—Not appressed.

*Surface*.—Slightly pubescent.

*Color*.—White [263. White].

Flowers: Perfect, complete, perigynous, usually a single pistil, typically twenty-eight or more stamens, five sepals and petal locations alternately positioned.

*Average flower diameter.*—1⅛" [28.6 mm.].

*Average flower depth.*—⅜" [9.5 mm.] when fully open.

*Average pedicel length.*—⅛" [3.2 mm.].

*Number of petals.*—Five, no double blossoms observed.

*Petal shape.*—Oval.

*Petal margin.*—Entire, smooth to somewhat wavy.

*Average petal diameter.*—7/16" [11.1 mm.].

*Average petal length.*—9/16" [14.3 mm.].

*Petal apex.*—Rounded.

*Petal base.*—Rounded.

*Petal color.*—White [263. White] on both sides.

*Anther color.*—Light orange yellow [70. l.OY].

*Pollen production.*—Moderate, bee enticing.

*Pollen color.*—Strong yellow [84. s.Y].

*Stigma color.*—Light greenish yellow [101. l.gY].

*Stigma position.*—Located slightly below the surrounding anthers.

*Sepal color.*—Light yellow green [119. l.YG] on both sides.

*Sepal length.*—7/32" [5.6 mm.].

*Sepal width.*—5/32" [4.0 mm.].

*Sepal apex.*—Rounded to elliptical to match the width and length.

*Sepal margin.*—Fairly smooth, with slight serration toward the apex.

*Average pistil length.*— 9/16" [14.3 mm.].

*Average stamen length.*— 7/16" [11.1 mm.].

*Ovary.*—Smooth.

*Fragrance.*—Moderate.

*Blooming period.*—Starts early and continues beyond the mid seasonal blooming varieties, beginning three days before 'Yummygem' (U.S. Plant Pat. No. 15,809) plum.

*Onset of bloom.*—One percent on Feb. 10, 2015.

*Date of full bloom.*—Mar. 5, 2015.

*Duration of bloom.*—Very long, lasting from two to five weeks, dependent on ambient temperatures.

*Bloom density.*—Very heavy.

*Number per cluster.*—Typically 3 or 4, up to 10 observed.

FRUIT

Maturity when described: Firm ripe, Oct. 27, 2015.

Date of first picking: Oct. 16, 2015.

Date of last picking: Nov. 5, 2015.

Size: Uniform, medium.

*Average diameter axially.*—2 5/16" [58.7 mm.].

*Average diameter across suture plane.*—2 11/16" [68.3 mm.].

*Average diameter across cheek plane.*—2 13/16" [71.4 mm.].

*Typical weight.*—6.2 ounces [176 grams].

Form: Mostly uniform, symmetrical, oblate.

*Longitudinal section form.*—Oblate.

*Transverse section through diameter.*—Round.

Suture: A shallow groove extending from the base to the pistil point.

Ventral surface: Rounded, very slightly lipped toward the base.

Lips: Equal.

Cavity: Flaring, circular.

*Depth.*—½" [12.7 mm.].

*Breadth.*—1⅛" [28.6 mm.].

Base: Truncate, cordate when viewed parallel to the suture.

Apex: Rounded.

Pistil point: An inconspicuous Brilliant orange yellow [67. brill.OY] dot located at the end of the suture.

Stem: Medium.

*Average length.*—7/16" [11.1 mm.].

*Average width.*—⅛" [3.2 mm.].

Skin:

*Thickness.*—Medium.

*Surface.*—Smooth.

*Tenacity.*—Tenacious to flesh.

*Astringency.*—Slight.

*Tendency to crack.*—None observed.

*Color.*—Very deep red [14. v.deep R] over a Vivid red [11. v.R] background with moderate Light orange yellow [70. l.OY] freckling throughout.

*Lenticels.*—Number Per Square Inch: About 180 toward the apex. Average diameter: ¼8" [0.5 mm].

*Bloom.*—Moderate to heavy.

Flesh:

*Color.*—Brilliant yellow [83. brill.Y] toward the skin smoothly blending to Vivid yellow [82. v.Y] toward the stone.

*Surface of pit cavity.*—Covered with very short Light orange yellow [70. l.OY] fibers.

*Amygdalin.*—Moderate.

*Juice.*—Abundant, rich.

*Texture.*—Firm, crisp, meaty.

*Fibers.*—Abundant, fine, tender.

*Ripens.*—Fairly even.

*Flavor.*—A tasty blend of acid and sugar, typically 22 to 24 brix.

*Aroma.*—Slight.

*Eating quality.*—Excellent.

STONE

Type: Freestone.

Form: Oval.

Hilum: Narrow.

Base: Rounded.

Apex: Acute, with an average angle of 45 degrees and a 1/32" [0.8 mm.] tip.

Sides: Mostly equal.

Ridges: Jagged.

External color of stone: Strong yellowish brown [74. s.yBr].

Pit wall color when cracked: Light yellowish brown [76. l.yBr].

Cavity surface color: Dark orange yellow [72. d.OY].

Average pit wall thickness: ⅛" [3.2 mm.]

Average length: 1" [25.4 mm.].

Average width: 13/16" [20.6 mm.].

Average breadth: ½" [12.7 mm.].

Tendency to split: None observed.

Kernel:

*Form.*—Oval.

*Pellicle color.*—Moderate yellowish brown [77. m.yBr].

*Skin color.*—Dark orange yellow [72. d.OY].

*Vein color.*—Moderate yellowish brown [77. m.yBr].

*Taste.*—Bitter.

*Viable.*—Yes.

*Average length.*—½" [12.7 mm.].
*Average width.*—7/16" [11.1 mm.].
*Amygdalin.*—Abundant.

USE

Market: Fresh market and long distance shipping.
Keeping quality: Excellent. Fruit quality observed to remain in good condition in after 21 days in standard cold room at 36° Fahrenheit [2° Celsius].
Shipping quality: Excellent.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, that is most similar to 'September Yummy' (U.S. Plant Pat. No. 14,220) plum by having a large tree, by being self-unfruitful, and by producing plums that are nearly full red with moderate freckling in skin color, mostly yellow in flesh color, juicy, firm in texture, but is distinguished therefrom by being more irregular in setting and by producing plums that are sweeter in flavor, that are oblate instead of globose in shape, and that ripen about thirty days later.

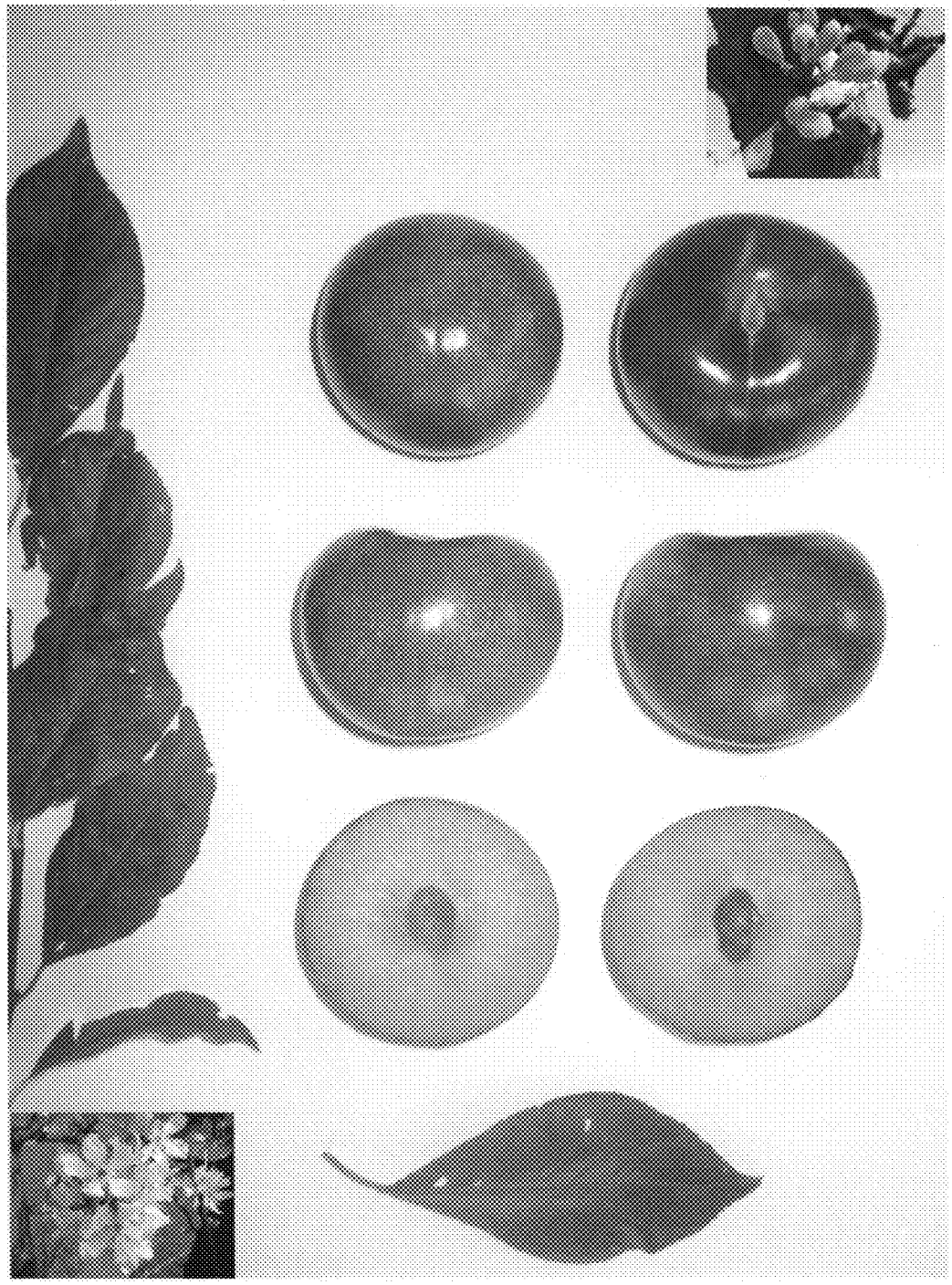

* * * * *